(12) United States Patent
Abe (10) Patent No.: US 9,901,485 B2
(45) Date of Patent: Feb. 27, 2018

(54) OPHTHALMIC LASER TREATMENT APPARATUS

(71) Applicant: NIDEK CO., LTD., Gamagori-shi, Aichi (JP)

(72) Inventor: Hitoshi Abe, Okazaki (JP)

(73) Assignee: NIDEK CO., LTD., Gamagori-shi (JP)

( * ) Notice: Subject to any disclaimer, the term of this patent is extended or adjusted under 35 U.S.C. 154(b) by 499 days.

(21) Appl. No.: 14/032,554

(22) Filed: Sep. 20, 2013

(65) Prior Publication Data
US 2014/0094783 A1    Apr. 3, 2014

(30) Foreign Application Priority Data
Sep. 28, 2012   (JP) .................. 2012-218634

(51) Int. Cl.
*A61F 9/008*    (2006.01)

(52) U.S. Cl.
CPC ...... *A61F 9/00823* (2013.01); *A61F 9/00821* (2013.01); *A61F 2009/00897* (2013.01)

(58) Field of Classification Search
CPC ................................ A61F 9/008–2009/00897
USPC ........................................ 606/2, 4–6, 10–11
See application file for complete search history.

(56) References Cited

U.S. PATENT DOCUMENTS

| | | | | |
|---|---|---|---|---|
| 5,971,978 A | * | 10/1999 | Mukai | ............ A61B 18/203 606/11 |
| 2007/0129775 A1 | | 6/2007 | Mordaunt et al. | |
| 2008/0015553 A1 | | 1/2008 | Zacharias | |
| 2009/0161826 A1 | * | 6/2009 | Gertner | ................ A61N 5/1017 378/65 |
| 2011/0245816 A1 | * | 10/2011 | Abe | ............... A61F 9/00821 606/4 |
| 2012/0184857 A1 | | 7/2012 | Yokosuka | |
| 2013/0317570 A1 | * | 11/2013 | Luttrull | ............... A61F 9/00821 607/89 |

(Continued)

FOREIGN PATENT DOCUMENTS

| | | |
|---|---|---|
| EP | 2 371 327 A1 | 10/2011 |
| EP | 2 371 328 A1 | 10/2011 |
| JP | A-2009-514564 | 4/2009 |

OTHER PUBLICATIONS

Dec. 20, 2013 Extended European Search Report issued in European Patent Application No. 13185771.6.

*Primary Examiner* — Gary Jackson
*Assistant Examiner* — Jonathan Kuo
(74) *Attorney, Agent, or Firm* — Oliff PLC (57) ABSTRACT

An ophthalmic laser treatment apparatus includes: an irradiation optical system including an optical scanner for two-dimensionally scanning spots of a treatment laser beam and an aiming beam on eye tissue; a control unit to control the irradiation optical system to irradiate the treatment beam to a spot position based on an irradiation pattern of spots for treatment beam irradiation and based on an aiming rule associated with the irradiation pattern to irradiate the aiming beam to indicate the treatment beam spot position; and a movement unit to move an irradiation position of each beam. The control unit irradiates the treatment beam to a sequence of spots from a n-th position to a m-th position in association with the irradiation pattern, and then controls the movement unit and irradiates the aiming beam based on the aiming rule to a position different from the spot position just irradiated by the treatment beam.

16 Claims, 5 Drawing Sheets

(56) References Cited

U.S. PATENT DOCUMENTS

2016/0346126 A1* 12/2016 Luttrull ................ A61N 5/0613
2017/0035612 A1*  2/2017 Luttrull ................ A61N 5/0613
2017/0319383 A1* 11/2017 Luttrull ................. A61F 9/008

* cited by examiner

OPHTHALMIC LASER TREATMENT APPARATUS

CROSS-REFERENCE TO RELATED APPLICATIONS

This application is based upon and claims the benefit of priority from the prior Japanese Patent Application No. 2012-218634, filed Sep. 28, 2012, the entire contents of which are incorporated herein by reference.

BACKGROUND OF THE INVENTION

Field of the Invention

The present invention relates to an ophthalmic laser treatment apparatus to irradiate a laser beam for treatment to an eye of a patient.

Related Art

One example of ophthalmic laser treatment apparatus is known as a photocoagulation apparatus. For photocoagulation treatment (e.g., panretinal photocoagulation treatment), a treatment laser beam is irradiated spot by spot to a fundus of a patient's eye to thermally coagulate a wide area of tissues. In recent years, there is known an apparatus provided with an optical scanner including a galvano mirror and others to sequentially irradiate a treatment laser beam based on an irradiation pattern consisting of a plurality of arranged spots (e.g., see Patent Document 1). In the treatment using such an apparatus, a pattern consisting of spots arranged in a square matrix of 3×3, for example, is used for irradiation of a number of spots. At that time, a wide range of the fundus is irradiated by spacing all the spots almost uniformly.

RELATED ART DOCUMENTS

Patent Documents

Patent Document 1: Japanese Translation of a PCT International Application Publication No. 2009-514564A

SUMMARY OF INVENTION

Problems to be Solved by the Invention

As described above, when a wide range of a patient's eye is to be irradiated by a treatment laser beam, an operator has to adjust the position of the apparatus every time after the irradiation of the treatment laser beam is terminated. This is troublesome. To be concrete, a slit lamp incorporating a laser delivery unit has to be wholly moved up and down or right and left every time after the irradiation of the treatment laser beam in a sequence of spots based on the irradiation pattern is terminated.

The present invention has been made in view of the circumstances to solve the above problems and has a purpose to provide an ophthalmic laser treatment apparatus capable of irradiating a wide area of a patient's eye based on an irradiation pattern while allowing an operator to observe the eye.

Means of Solving the Problems

To achieve the above purpose, one aspect of the invention provides an ophthalmic laser treatment apparatus including: an irradiation optical system including an optical scanner for two-dimensionally scanning a spot of a treatment laser beam from a laser light source and a spot of an aiming beam from an aiming light source on a tissue of a patient's eye; a control unit configured to control the irradiation optical system to irradiate the treatment laser beam to a spot position based on an irradiation pattern in which a plurality of spots for irradiation of the treatment laser beam are arranged, the control unit being arranged to control the irradiation optical system based on an aiming rule associated with the irradiation pattern to irradiate the aiming beam to the spot position to indicate the spot position for irradiation of the treatment laser beam; and a movement unit configured to move an irradiation position of the treatment laser beam and the aiming beam, wherein the control unit irradiates the treatment laser beam to a sequence of spots from a n-th spot position (n is a natural number) to a m-th spot position (m is a larger natural number than n), determined in association with the irradiation pattern, and then controls the movement unit and irradiates the aiming beam based on the aiming rule to a position different from the spot position just irradiated by the treatment laser beam.

Effects of the Invention

According to the present invention, it is possible to efficiently irradiate a treatment laser beam over a wide area of a patient's eye.

DESCRIPTION OF EMBODIMENTS

Figure 1:
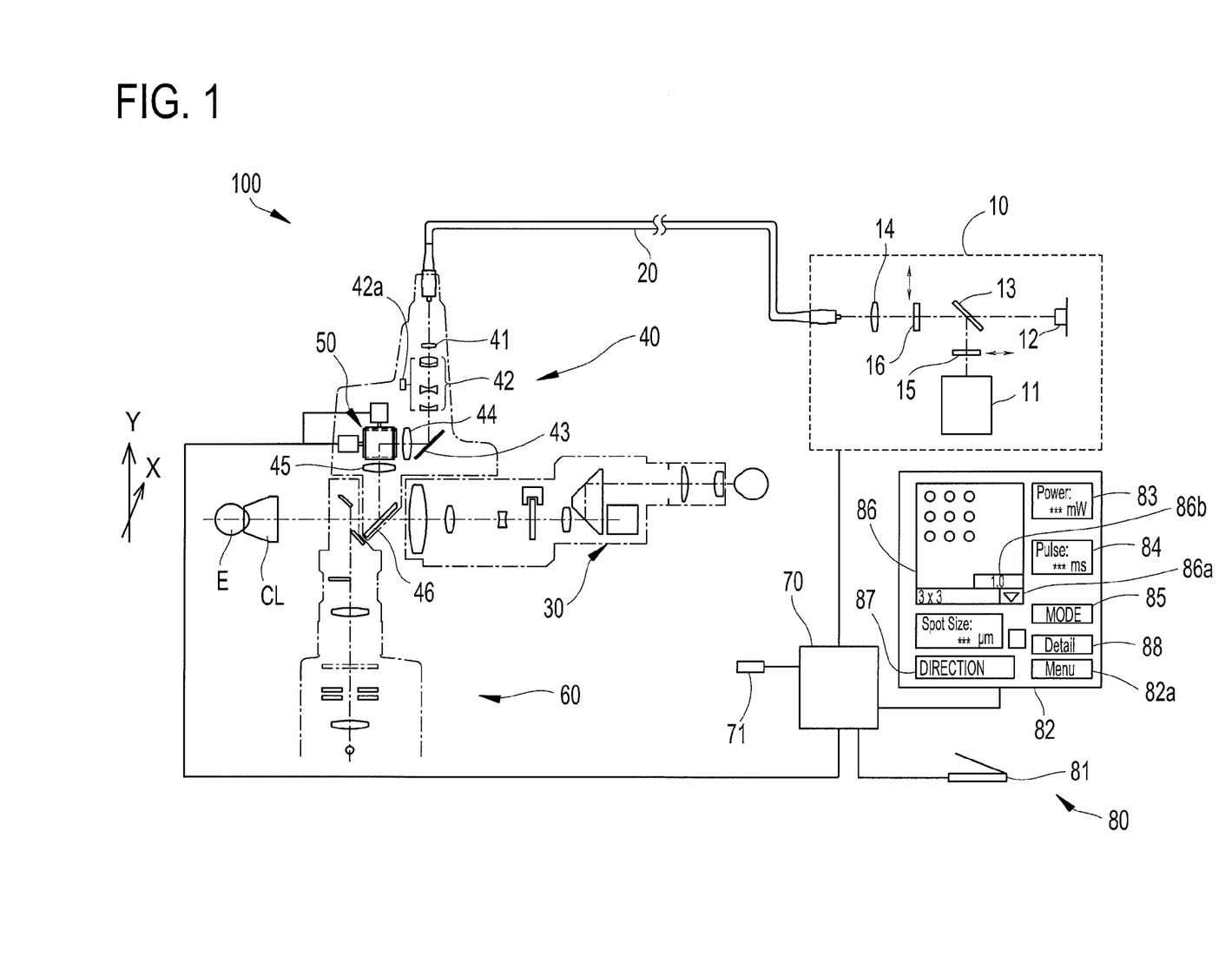
FIG. 1 is a schematic configuration diagram of optical systems and a control system of an ophthalmic laser treatment apparatus.

A detailed description of a preferred embodiment of the present invention will now be given referring to the accompanying drawings. FIG. 1 is a schematic configuration diagram showing optical systems and a control system of an ophthalmic laser treatment apparatus. The ophthalmic laser treatment apparatus of the present embodiment is a photocoagulation apparatus configured to irradiate a treatment laser beam to a fundus of a patient's eye to coagulate its tissues.

An ophthalmic laser treatment apparatus 100 includes a laser source unit 10, a laser irradiation optical system (unit) 40, an observation optical system (unit) 30, an illumination optical system (unit) 60, a control unit 70, and an operation unit 80. The observation optical system 30 and the illumination optical system 60 form a slit lamp (a slit lamp microscope). The laser irradiation optical system 40 is attached to the slit lamp. The laser source unit 10 includes a treatment laser source 11, an aiming light source 12, a beam combiner 13, a condensing lens 14, shutters 15 and 16.

The treatment laser source 11 emits a laser beam of a wavelength suitable for treatment. In the present embodiment, the light source 11 is configured to emit a laser beam of a wavelength in visible region, e.g., 532 nm (green), 577 nm (yellow), and others, to allow the energy of a laser beam to be absorbed by a fundus. The aiming light source 12 emits an aiming beam to make an operator see a position (spot) to be irradiated by the treatment laser beam. In the present embodiment, the aiming beam has a wavelength in visible region so as to be visible to the naked eyes of the operator. Herein, the aiming beam is set to a wavelength different from the treatment laser beam, e.g., set to 640 nm (red). Accordingly, even if the observation optical system 30 includes an operator protection filter for attenuating the treatment laser beam, the operator can easily see the irradiation position of the treatment laser beam. The aiming light source 12 used herein is for example a laser diode (LD) that emits a red laser beam, but is not limited thereto.

The beam combiner 13 serves to combine the treatment laser beam and the aiming beam (make the beams coaxial with each other). The beam combiner 13 for example reflects most part of the treatment laser beam, while transmits the aiming beam. Thus, the beam combiner 13 of the present embodiment is a dichroic mirror. The laser beams combined by the beam combiner 13 are condensed by the condensing lens 14 and made to enter an optical fiber 20 whereby the laser beams are delivered to the laser irradiation optical system 40.

The shutter 15 is provided between the treatment laser source 11 and the beam combiner 13. The shutter 15 is used to block off the treatment laser beam. The shutter 15 includes a shield plate and a drive mechanism for the shield plate and is configured to move the shield plate into and out of an optical path in response to a command signal. The shutter 16 is placed downstream of the beam combiner 13 and between the beam combiner 13 and the condensing lens 14. The shutter 16 is identical in configuration to the shutter 15 and used to block off the aiming beam and the treatment laser beam. The shutter 16 is a safety shutter that is closed in case the apparatus is failed, but may also be used to allow and block irradiation of the aiming beam during scanning of the aiming beam. Further, the shutter 16 may also be used to allow and block irradiation of the treatment laser beam. Those shutters may be replaced with a galvano mirror having the function of changing (deflecting) an optical path and an acousto-optic modulator.

The laser irradiation optical system (a laser delivery) 40 includes a relay lens 41, zoom lenses (a lens group) 42, a mirror 43, a collimator lens 44, an optical scanner (a scanning part) 50, an objective lens 45, and a reflection mirror (a last mirror) 46. An emission end of the fiber 20 is located upstream of the laser irradiation optical system 40. The fiber 20 delivers a laser beam from the laser source unit 10 to the laser irradiation optical system 40. The zoom lenses (lens group) 42 include a plurality of lenses movable along an optical axis to change a spot size of the laser source on the fundus. The reflection mirror 46 is a beam combining member to combine the optical path of the observation optical system 30 and the optical axis of the laser beam. The reflection mirror 46 is placed between optical paths for right and left eyes in the observation optical system 30.

The optical scanner 50 has the functioning of two-dimensionally scanning (moving) the laser beam (the treatment laser beam and the aiming beam) on the fundus. The optical scanner 50 also has the functioning of deflecting the optical axis (optical path) of the treatment laser beam and others to change a spot position of the laser beam on the fundus. By the optical scanner 50, an irradiation direction (an irradiation position) of the laser beam is adjusted.

In the present embodiment, the optical scanner 50 is also used as a movement unit (a movement optical system) for moving an irradiation position of the treatment laser beam and an irradiation position of the aiming beam on the fundus. In other words, the optical scanner 50 moves a pattern (an aiming pattern) in which spots of the aiming beam to be irradiated according to an irradiation pattern mentioned later are arranged.

The optical scanner 50 includes a first scan unit for scanning a laser beam in an X direction (a right-and-left (horizontal) direction with respect to a patient's eye E, i.e., a perpendicular direction to the drawing sheet of FIG. 1) and a second scan unit for scanning the laser beam in a Y direction (an up-and-down (vertical) direction with respect to the patient's eye E, i.e., a vertical direction in FIG. 1). The first and second scan units of the present embodiment are respectively formed of galvano mirror units. Herein, two galvano mirror units are placed so that the rotation axes of respective mirrors intersect with each other at right angles. The optical scanner has only to be configured to scan (move) a laser beam (its optical axis) in two dimensions (in the X and Y directions) on the fundus. It may also consist of a polygon mirror for X-direction scan and a galvano mirror for Y-direction scan. As another alternative, two resonant mirrors may be used for X-direction scan and Y-direction scan.

The zoom lenses 42 are retained in a lens cam not illustrated. When the lens cam is rotated by operation of an operator, each zoom lens 42 is moved along the optical axis. As each zoom lens 42 is moved, a spot size of the laser beam (a spot diameter on the fundus) is changed sequentially in a range of 50 to 500 μm. The spot size is a magnifying power of an emission end face of the fiber 20, which is a magnifying power of 1× to 10×. The position of each zoom lens 42 is detected by an encoder 42a attached to the lens cam. The control unit 70 receives a positional information (a detection signal) of each lens from the encoder 42a to obtain the spot size of a laser beam.

The optical scanner 50 is controlled based on a command signal from the control unit 70 to direct the laser beam (spot) to form a two-dimensional pattern on a target plane. The reflection mirror 46 may be connected to a mechanism (a hand-operated manipulator) not illustrated to tilt (deflect) the optical axis of the laser beam two-dimensionally by operation of an operator.

A contact lens CL is placed in contact with a cornea of the eye E. This contact lens CL serves to cancel the refractive powers of the cornea and a crystalline lens of the eye E. The contact lens CL forms a conjugate plane of the fundus of the eye E between the contact lens CL and the mirror 46.

The laser beam emitted from the optical fiber 20 passes through the relay lens 41, zoom lenses 42, mirror 43, and collimator lens 44, and enters the optical scanner 50. The laser beam is deflected by the optical scanner 50 and emitted through the objective lens 45. This laser beam is reflected by the mirror 46 toward the eye E and then is introduced to the fundus (the target plane) through the contact lens CL.

The observation optical system 30 includes an objective lens, a variable power optical system, an operator-protection filter, an erect prism, a field diaphragm, and eyepieces. The operator-protection filter includes a filter and an insertion/removal mechanism for inserting/removing the filter in/out of an observation optical path. The filter is configured to be inserted in the observation optical path at least while the treatment laser beam is being irradiated. The illumination optical system 60 includes an illumination light source, a condenser lens, a slit plate, and a projection lens. The slit plate is formed with an aperture to project illumination light in a slit form. The slit plate is provided with a mechanism for changing the width of the aperture. Furthermore, the slit plate is horizontally rotatable (rotatable about an illumination optical axis). By operation of the slit plate, the width and the angle of the slit light to be projected on the fundus can be adjusted. An operator observes the fundus illuminated by the slit light from the illumination optical system 60 and performs laser irradiation.

The control unit 70 that controls over the apparatus 100 is connected to the treatment laser source 11, the aiming light source 12, the shutters 15 and 16, the encoder 42a, the optical scanner 50, a memory 71, the operation unit 80, and others. As the control unit 70, a central processing unit (CPU) is used. The memory 71 serving as a storage unit stores irradiation patterns, aiming rules, surgical conditions, control programs of the apparatus, and others.

The operation unit 80 is provided with a foot switch 81 serving as a trigger input unit for inputting a signal to trigger the irradiation of the treatment laser beam and a display 82 for setting and displaying laser irradiation conditions and others. The display 82 is a touch panel and used as both a display means and a setting (input) means.

The display 82 is provided with various setting parts and panel switches for setting (inputting setting signals). The display 82 functions as a graphical user interface configured to allow a user (an operator) to visually check and set laser irradiation conditions and others. The display 82 is configured to set and display the following irradiation condition items.

The display 82 includes an output power setting part 83, an irradiation time setting part 84, a movement mode setting part 85, a pattern setting part 86, a movement direction setting part 87, a detail setting switch 88, and a menu switch 82a. The pattern setting part 86 includes a switch 86a and a spot interval setting part 86b. A numeral value and others can be set or chosen by touching on each of the items on the display 82. The set conditions such as a numeral value and others are stored in the memory 71.

The output power setting part 83 enables setting of output (power) of the treatment laser beam. The irradiation time setting part 84 enables setting of irradiation time (pulse width) of the treatment laser beam. The movement mode setting part 85 enables setting of a movement mode of an irradiation position of the aiming beam. On this movement mode setting part 85, two mode is selectively set. The pattern setting part 86 enables setting of an irradiation pattern of the treatment laser beam. When the switch 86a is touched, a pull-down menu appears to display selectable options. The number of spots can be increased or decreased by touch operation and others on the pattern setting part 86. The spot interval setting part 86b enables setting of a spot interval of an irradiation pattern. The movement direction setting part 87 enables setting of the movement direction of an irradiation position of the aiming beam (the whole pattern consisting of arranged spots of the aiming beam) after a series of irradiation of the treatment laser beam. The detail setting switch 88 enables setting of detailed conditions. The menu switch 82a is a switch to invoke other setting parts and so on.

The spot interval setting part 86b is a switch to set an interval (distance) between spots in an irradiation pattern and functions as a spot interval input unit for inputting a spot interval to the control unit 70. The spot interval in this embodiment is a shortest distance between edges of adjacent spots. Assuming that an interval corresponding to one spot is 1.0, the spot interval is selectable from 0.5 to 2.0 in 25 steps. In the present embodiment, the spot interval is set at 1.0.

With the movement direction setting part 87, the movement direction is selectively set from two types; from above to below along the up-and-down direction (Y direction) and from left to right along the left-and-right direction (X direction). Herein, the movement direction corresponds to a longitudinal direction of slit light (slit illumination light). The movement direction setting part 87 functions as a movement direction input unit for inputting the movement direction of an irradiation position of the aiming beam to the control unit 70. Herein, the up-and-down direction is set.

Figure 2A:
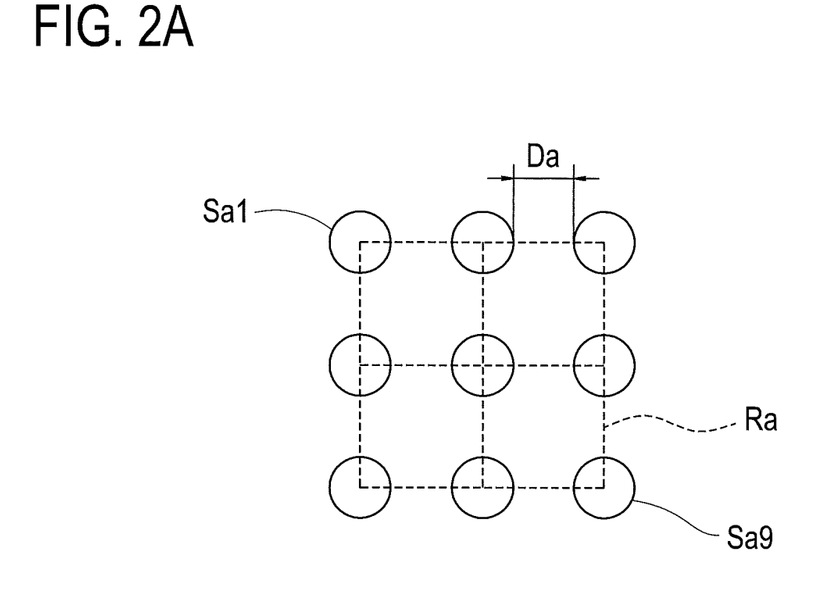
FIGS. 2A and 2B are diagrams to explain irradiation patterns of 3×3.
Figure 2B:
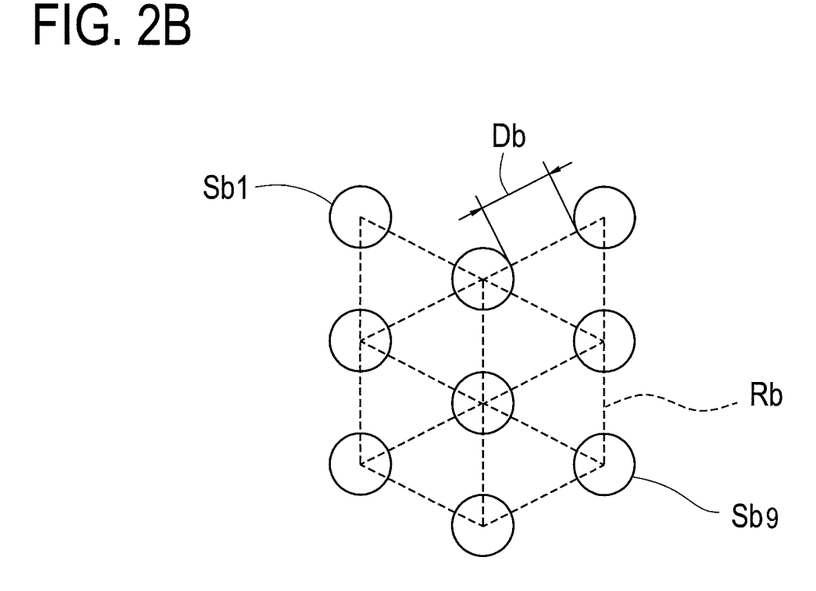

Next, the irradiation patterns and the irradiation of the aiming beam will be explained. FIGS. 2A and 2B show the irradiation patterns. This irradiation pattern is a pattern in which irradiation spot positions of the treatment laser beam are arranged. In the irradiation pattern of the present embodiment, the spots are spaced at a distance from each other. The aiming beam is irradiated to the spot positions associated with the irradiation pattern to indicate the irradiation pattern in symbolic fashion to allow an operator to visually recognize the irradiation spot positions of the treatment laser beam. In the present embodiment, the aiming beam is irradiated to the same spot positions as the irradiation position (irradiation planned positions) of the treatment laser beam.

In the irradiation pattern, the spots are arranged based on a rule (e.g., a geometric configuration). This irradiation pattern may include a pattern of spots arranged in a square matrix of 2×2, 3×3, 4×4 or others (a square pattern, see FIG. 2A), a pattern of spots arranged so that an even-numbered spot column of a square pattern is displaced in a staggered matrix (a staggered pattern, see FIG. 2B), a pattern of spots arranged in a circular arc form (a circular arc pattern), a pattern of spots arranged in an outer circumferential direction and an inner circumferential direction to form a fan-like form (a fan-like pattern), a pattern of spots arranged in a circular form (a circular pattern), a segmental pattern of the circular pattern (a circular segmental pattern), a linear pattern of spots arranged in a linear form, and other patterns. These irradiation patterns are prepared by an apparatus manufacturer and stored in the memory 71.

The aiming (operation) of the present embodiment is performed based on the aiming rule explained below. In the aiming, while the treatment laser beam is not yet irradiated (i.e., during alignment operation), the spots of the aiming beam are appropriately blinked to make an operator easily check the condition of the fundus under the spots. To be concrete, the aiming beam is irradiated to the spots of the irradiation pattern divided into a plurality of groups so that each spot group is blinked at a required time interval. The spots may also be divided into groups with some spots of one group overlapping spots of another group. The required time interval in the present embodiment is defined as the period of time in which the spots are invisible to the operator as if they are turned off from group to group. In other words, this time interval allows the operator to observe the condition under the spots. Each spot group of the divided irradiation pattern and the turn-on (turn-off) time of each group are defined as an aiming rule. The aiming rule is stored in the memory 71 as an aiming control program. The control unit 70 irradiates the aiming beam according to the aiming rule. Such aiming is disclosed in JP 2011-224345A. Refer to this publication as an example of the aiming.

The aiming rule has only to be determined to allow an operator to recognize an irradiation position of a treatment laser beam. Accordingly, various aiming rules are available.

For example, the aiming rule may be configured to continuously light up all the spots of the irradiation pattern or to blink all the spots.

Furthermore, the aiming beam does not always need to be irradiated at the spot positions of the treatment laser beam. For instance, the aiming beam may also be irradiated only at spot positions on an outermost circumference of the irradiation pattern. As another alternative, the aiming beam may be irradiated to indicate an outline and a region of the irradiation pattern. For a square pattern, for example, the aiming beam is irradiated continuously to scan an outline (a frame) of the square pattern or the aiming beam is irradiated to indicate a cross shape representing the region of the square pattern.

Arrangement rules of spots of the irradiation patterns are explained referring to FIGS. 2A and 2B. These figures exemplify a square pattern and a staggered pattern respectively. Specifically, FIG. 2A shows a square pattern of 3×3 spots and FIG. 2B shows a staggered pattern of 3×3 spots.

As shown in FIG. 2A, the spots are arranged in a regular manner so that the center point of each spot is located at an apex of each cell of a grid Ra indicated by a dotted line. The grid Ra is a 3×3 square grid. Thus, its irradiation pattern (the irradiation of the aiming beam is identical) is a square pattern. According to the grid Ra, the arrangement rule of spots of the treatment laser beam and the aiming beam is specified. The grid interval of the grid Ra is determined so that an interval between adjacent spots (herein, in up-and-down and right-and-left directions) is a predetermined distance (length). In this embodiment, a spot interval Da is determined assuming that the interval of the grid Ra (grid interval) is one spot so that a distance between adjacent spots corresponds to one spot. In the up-and-down and right-and-left directions of the square pattern, the spot interval is uniform between any adjacent spots. Accordingly, when the treatment laser beam is irradiated in the square pattern, heat diffusion around each spot is homogenized, thus uniformizing coagulation on each spot and between spots. Thus, a region (herein, a region of a 3×3 square matrix) irradiated by the treatment laser beam is almost homogeneously (uniformly) treated.

During treatment, the treatment laser beam is sequentially irradiated to the predetermined spot positions of the irradiation pattern. In the case of the 3×3 square pattern, upon input of a trigger signal from the foot switch 81, the treatment laser beam is irradiated at a sequence of spots from a n-th spot position to a m-th spot position determined in association with the irradiation pattern (herein, the square pattern). Herein, n is a natural number (n=1, 2, . . . , N) and m is a natural number larger than n (m>n, m=2, 3, . . . , M). Therefore, in response to the trigger signal, the treatment laser beam is irradiated in at least two spots. In the present embodiment, when the trigger signal is input by the operator, the treatment laser beam is irradiated to a sequence of the n-th to m-th spots, in which the ordinal numbers, n and m, are preset in association with the irradiation pattern. This association is stored in the memory 71 as an irradiation control program of the treatment laser beam. Preferably, the n-th and m-th spots are set to fall within a period of time in which an eyeball or the like does not move during irradiation of the treatment laser beam in a series of irradiation of the treatment laser beam.

For instance, the n-th and m-th spots are set in the following manner. The n-th spot associated with the 3×3 square pattern is a start spot (a first spot). The m-th spot is a last spot (a ninth spot). Accordingly, through a series of irradiation of the treatment laser beam, the treatment laser beam is irradiated to all the spots of the irradiation pattern.

The treatment laser beam is irradiated in turn from a spot Sa1 corresponding to a first spot position of the square pattern toward a spot Sa9 corresponding to a ninth spot position. Scanning of a sequence of spots is performed from one spot to an adjacent spot as if the laser beam traces a numeral "2". In the present embodiment, a period of time for irradiation of a sequence of spots of the treatment laser beam is shortened to reduce the influence that causes the patient's eye to move during irradiation of the treatment laser beam. Specifically, after irradiation of the spot Sa1, the treatment laser beam is irradiated to an adjacent spot (on the right in the figure) to the spot Sa1. The irradiation time duration of the treatment laser beam per one spot is set to about 5 to 50 ms, e.g., 20 ms in the present embodiment. Accordingly, a series of irradiation of treatment laser beam is 0.2 seconds or shorter. A preferable time duration of a series of irradiation of the treatment laser beam is 1 second or less. The above procedure (flow) is repeated to sequentially irradiate the treatment laser beam at one spot at a time from the spot Sa1 to the spot Sa9. As above, the positions on the tissues (spots) corresponding to the irradiation pattern (the square pattern) are the positions of a series of irradiation of the treatment laser beam.

The above square pattern is considered as effective in treating a wide area of the fundus. The square pattern can form a treatment region in an almost rectangle (square), so that a certain area (region) is substantially filled with a plurality of the square patterns without gaps.

In the above explanation, the treatment laser beam and others are sequentially irradiated from the n-th spot (herein, the start spot) to the m-th spot (herein, the last spot), but are not limited thereto. The terms "n-th" and "m-th" merely specify spot positions, but do not indicate the order of spots to be irradiated.

The staggered pattern in FIG. 2B will be explained below. The spots are regularly arranged so that the center point of each spot is located at an apex of a grid Rb indicated by a dotted line in the figure. The grid Rb is a 3×3 triangular grid (a hexagonal grid). This triangle form of the triangular grid is a regular triangle. Thus, the distance between the adjacent apexes of the grid Rb is uniform in any directions. Accordingly, in the staggered pattern, a spot interval Db between adjacent spots is constant in up and down directions and oblique directions (60° and 240°, and 120° and 300°). The spot interval Db is equal to the spot interval Da. In the staggered pattern defined by the grid Rb, all the spots adjacent to a certain spot are spaced by the same interval from the certain spot. This pattern can provide more expectation of homogenization of thermal coagulation than the square pattern. In the irradiation based on the staggered pattern, as with the square pattern, the treatment laser beam is sequentially irradiated from a spot Sb1 corresponding to a start spot position to a spot Sb9 corresponding to a last spot position.

In the staggered pattern of the present embodiment, the number of spots is set to be equal in every column (a vertical line in this embodiment) so as to allow the staggered patterns to be evenly arranged without gaps (all the spots are arranged at the same spot intervals). Further, the position of a predetermined column is displaced in a specific direction. For instance, the even-numbered (second) column is placed with a downward displacement from the odd-numbered (first and third) columns. Accordingly, the staggered pattern shown in FIG. 2B is convexed on a lower side and concaved on an upper side. A plurality of staggered patterns are arranged so that the adjacent patterns are placed with respective convex and concave shapes engaging with each other. Thus, the staggered patterns can be disposed so as to cover over the treatment region.

An irradiation manner of the aiming beam and the treatment laser beam in the staggered pattern is similar to that in the square pattern.

The aforementioned square pattern and staggered pattern may also be used in respective turned states (e.g., rotated about a center spot). They have only to be arranged so that the spots have an interrelationship based on the aforementioned grids.

Figure 3:
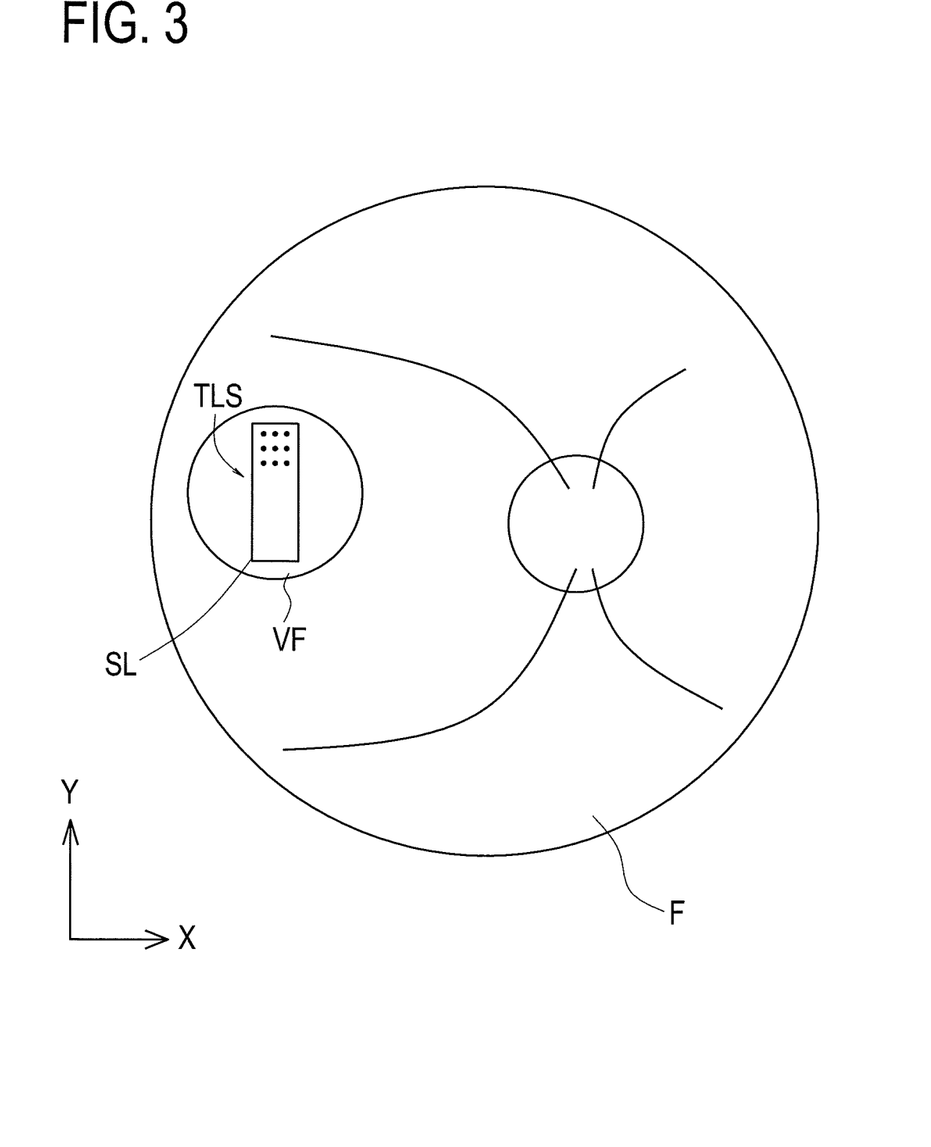
FIG. 3 is a schematic diagram of a fundus.

Next, photocoagulation treatment will be explained. FIG. 3 is a diagram showing a wide range of the fundus. On the fundus F, there are displayed a slit light SL directed (extending) in the up-and-down direction (Y direction) and an irradiated spot array TLS schematically representing the positions irradiated by the treatment laser beam. As a treatment method using a number of spots of a treatment laser beam over a wide range of the fundus, there is for example panretinal photocoagulation treatment (PRT). In PRT, a wide area other than a macula of the fundus F is subjected to coagulation. The PRT is performed by irradiating a treatment laser beam by hundreds to thousands of spots. During irradiation of the treatment laser beam, the fundus F is zoomed in to allow an operator to check an irradiation site. Laser irradiation is advanced within a magnified (narrow) visual field VF. Through the illumination optical system 60, the slit light SL is projected on the fundus F and the range of the visual field VF is observed through the observation optical system 30. The visual field VF at this time is wider by about a dozen to several-ten times than the lateral width of the slit light SL (FIG. 3 illustrates the visual field VF in a schematic form to facilitate explanation).

To irradiate the treatment laser beam over the whole fundus F, it is necessary to change a next irradiation region of the treatment laser beam after a laser irradiation work within the visual field VF is terminated. Further, after the treatment laser beam irradiation work within the whole visual field VF is terminated, the work is progressed after changing an observation region. In order to check the irradiation position of the treatment laser beam, the treatment laser beam has to be irradiated along the region illuminated by the slit light SL (herein, downward). FIG. 3 shows the spot array TLS including a plurality of spots of the treatment laser beam irradiated within the slit light SL.

When the treatment laser beam is to be irradiated along the slit light SL, for example, it is necessary to irradiate the laser beam in the square pattern or staggered pattern and then move the irradiation position of the treatment laser beam in the up-and-down direction. To be concrete, the observation optical system 30, the illumination optical system 60, and the laser irradiation optical system 40 (the whole slit lamp) are moved upward and downward (herein, downward) by operation of a joystick or the like. Every time after irradiation of a sequence of spots of the treatment laser beam (i.e., every time after irradiation of the treatment laser beam in one pattern), the operator is required to operate the observation optical system 30 and others. This is troublesome.

Figure 5A:
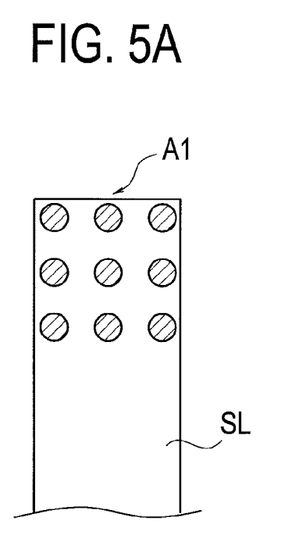
FIGS. 5A to 5C are diagrams to explain irradiation of a treatment laser beam and an aiming beam in an automatic mode.
Figure 5B:
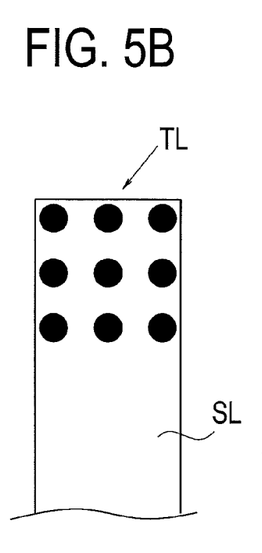
Figure 5C:
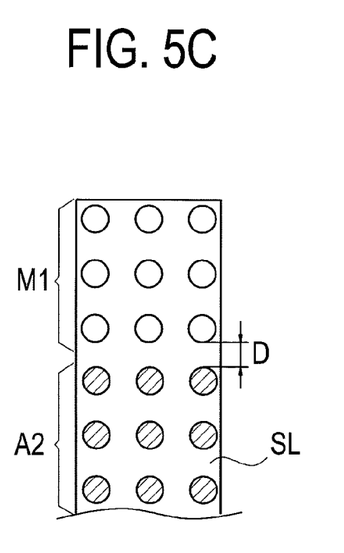
Figure 6:
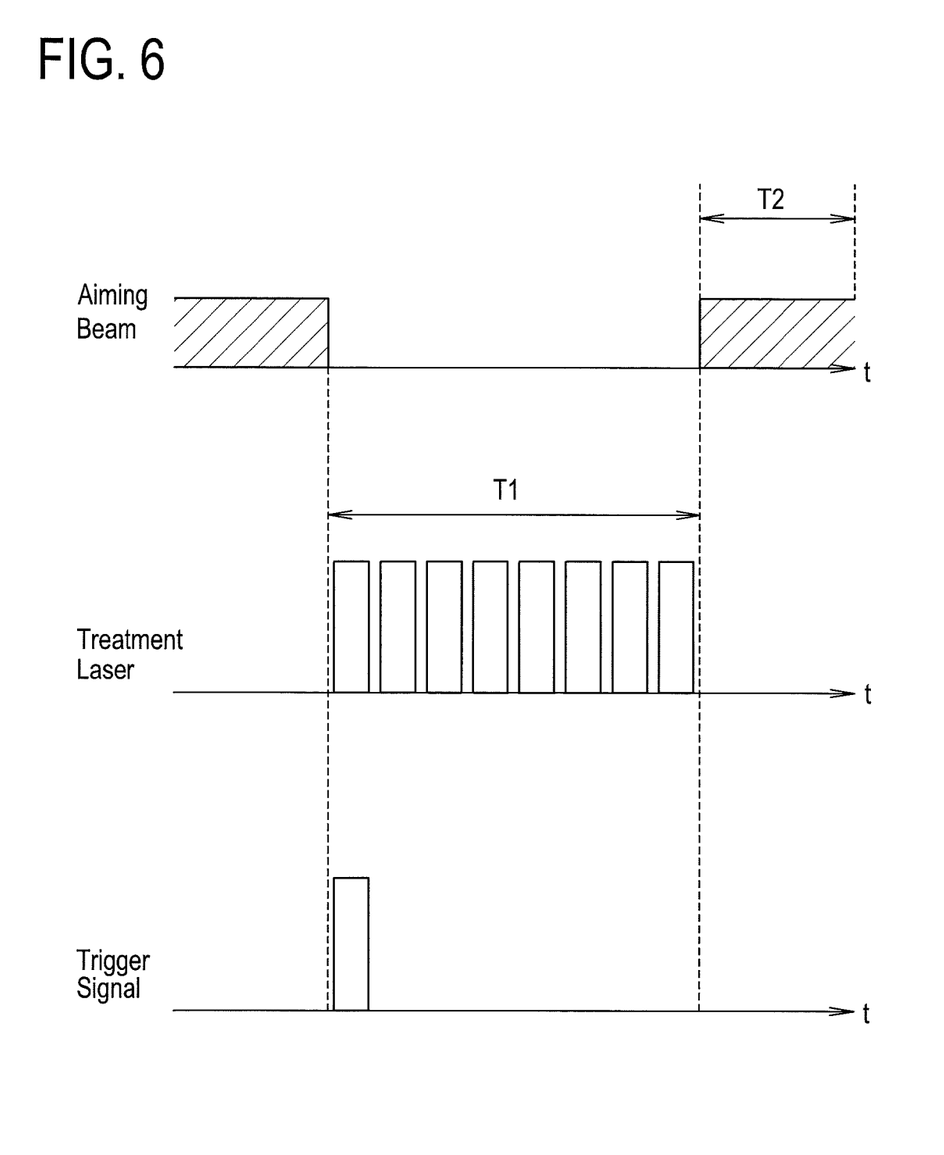
FIG. 6 is a timing chart of irradiation of a treatment laser beam and an aiming beam.

The irradiation of the treatment laser beam and the aiming beam based on the square pattern will be explained below. FIGS. 4A to 4C and FIGS. 5A to 5C are diagrams to explain movement of the irradiation positions of the aiming beam after irradiation of the treatment laser beam. FIG. 6 is a timing chart of irradiation of the treatment laser beam and the aiming beam.

FIGS. 4A to 4C and 5A to 5C show an example in which a treatment laser beam is irradiated, based on the 3×3 square pattern, to a site illuminated by the slit light SL extending in the up-and-down direction. Herein, the treatment laser beam is irradiated in correspondence with the square pattern from an upper side to a lower side in a region illuminated by the slit light SL.

The aiming states shown in FIGS. 4A to 4C and 5A to 5C are obtained based on one example of the aiming rule. They are exemplified as irradiating the aiming beam to the spot positions which will be irradiated later by the treatment laser beam.

The movement mode setting part 85 serves as a movement mode setting unit for setting a movement mode of the irradiation position of the aiming beam after irradiation of a sequence of spots of the treatment laser beam. The movement mode setting part 85 is configured to selectively set an automatic mode (a first movement mode) to move the irradiation position of the aiming beam to a position different from an irradiated position by the treatment laser beam after irradiation of a sequence of spots of the treatment laser beam and a manual mode (a second movement mode) in which the irradiation position of the aiming beam is not moved after irradiation of a sequence of spots of the treatment laser beam.

Figure 4A:
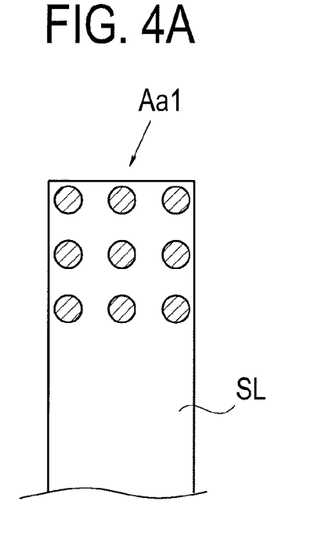
FIGS. 4A to 4C are diagrams to explain irradiation of a treatment laser beam and an aiming beam in a manual mode.
Figure 4B:
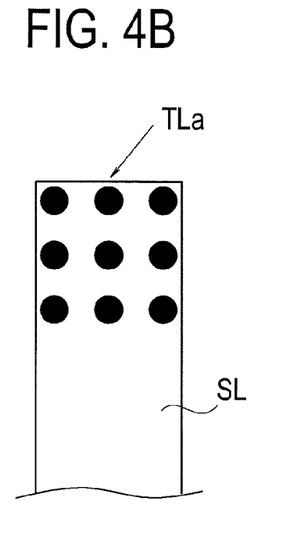
Figure 4C:
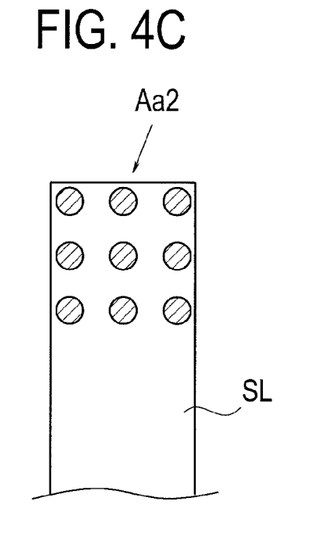

FIGS. 4A to 4C show an example of the manual mode. FIGS. 5A to 5C show an example of the automatic mode. In FIGS. 4A to 4C and 5A to 5C, the irradiation spots of the aiming beam are indicated by oblique lines, the irradiation spots (irradiated spots) of the treatment laser beam are filled in with black, and coagulation spots (spots alternated by heat) are filled in white. FIGS. 4A and 5A show a state under aiming (aiming condition), FIGS. 4B and 5B show a state under irradiation of the treatment laser beam, and FIGS. 4C and 5C show a state under aiming after irradiation of the treatment laser beam.

The manual mode is first explained. The aiming beam is irradiated to a region Aa1 representing an irradiation position of the aiming beam associated with the 3×3 square pattern. The aiming beam is sequentially irradiated based on the predetermined aiming rule corresponding to the square pattern. When the square pattern is set with the pattern setting part 86, a setting signal is transmitted to the control unit 70. Based on the setting signal and the control program (the aiming rule) stored in the memory 71, the control unit 70 controls the aiming light source 12, the optical scanner 50, and others to irradiate the aiming beam to the spot positions of the square pattern. Thus, the aiming beam is irradiated to the region Aa1 (see FIG. 4A).

When the foot switch 81 is depressed in a state of FIG. 4A, thereby triggering irradiation of the treatment laser beam, the state shifts (transitions) to the state of FIG. 4B. In response to the trigger signal from the foot switch 81, the control unit 70 controls the treatment laser source 11 and the optical scanner 50 to sequentially irradiate the treatment laser beam to the spot positions in 3×3 matrix in the region Aa1. Thus, the 3×3 spots irradiated by the treatment laser beam are formed in a region TLa.

After irradiation of a sequence of spots of the treatment laser beam is terminated, the state shifts to a state of FIG. 4C, in which the control unit 70 performs irradiation of the aiming beam again. At that time, the control unit 70 irradiates the aiming beam to a region Aa2 that is the same region as the region just irradiated by the treatment laser beam (i.e., the same position as the irradiation position of the aiming beam before irradiation of the treatment laser beam). The control unit 70 continues to irradiate the aiming beam to the region Aa2.

The manual mode is a mode of only irradiating the treatment laser beam to the spot positions of the aiming beam corresponding to the irradiation pattern. Accordingly, the irradiation positions of the aiming beam are not moved unless the optical systems are moved. Even after a series of irradiation of the treatment laser beam is terminated, the aiming beam is irradiated to the initial state, that is, to the spot positions just irradiated by the treatment laser beam. In the manual mode, therefore, the operator has to operate the joystick to move (operate) the irradiation optical system 40 downward every time after a series of irradiation of the treatment laser beam is terminated, as described above.

Next, the automatic mode will be explained. In a state of FIG. 5A, the aiming beam of the 3×3 square pattern (the aiming beam spot pattern) is irradiated to a region (a first region) A1. The aiming beam is irradiated based on the aiming rule corresponding to the predetermined square irradiation pattern. When the square pattern is set with the pattern setting part 86, a setting signal is transmitted to the control unit 70. Based on the setting signal and the control program (the aiming rule) stored in the memory 71, the control unit 70 controls the aiming light source 12, the optical scanner 50, and others, to irradiate the aiming beam. At that time, the control unit 70 sets the spot interval of the aiming beam to D in response to a signal representing the spot interval D set with the spot interval setting part 86b and the spot size from the encoder 42a.

When the foot switch 81 is depressed in the state of FIG. 5A, the treatment laser beam is irradiated, the state shifts to the state of FIG. 5B. In response to the trigger signal from the foot switch 81, the control unit 70 controls the treatment laser source 11 and the optical scanner 50 to sequentially irradiate the treatment laser beam to the 3×3 spot positions in the region A1. Accordingly, the 3×3 spots irradiated by the treatment laser beam are formed in the region TL.

After irradiation of a sequence of spots of the treatment laser beam is terminated, the state shifts to a state of FIG. 5C, in which the control unit 70 controls the aiming light source 12, the optical scanner 50, and others based on the movement direction (from above to below) set with the movement direction setting part 87 and the spot interval to irradiate the aiming beam in spots positions of a region (a second region) A2 below a region M1 (in the up-and-down direction) in which coagulation spots have been made. The control unit 70 irradiates the aiming beam in the spot positions different from the spot positions already irradiated by the treatment laser beam to prompt the operator to perform subsequent irradiation of the treatment laser beam. It should be noted that, in FIG. 5C, the coagulation spots thermally coagulated by the treatment laser beam are made in the spot positions irradiated by the treatment laser beam.

At that time, the control unit 70 performs irradiation of the aiming beam for at least a period of time allowing the operator to recognize the spot positions of the region A2, which details will be described later. In the present embodiment, the aiming beam is continuously irradiated at least for a period until the trigger signal for the treatment laser beam is input.

The region M1 (coincident with the region A1) and the region A2 are spaced by the spot interval D. To be concrete, taking notice of a spot of a lowermost line (a last line) in the region TL and a spot of an uppermost line (a first line) in the region A2, the irradiation position of the region A2 is moved to provide the spot interval D between the adjacent spots in the up-and-down direction (the movement direction). Specifically, the optical scanner 50 and others are controlled to arrange the spots of the aiming beam in a grid form (rule) of the square pattern associated with the spot interval D.

When the foot switch 81 is depressed in the state of FIG. 5C, the treatment laser beam is irradiated to the region A2. The irradiation position of the aiming beam is moved below the region just irradiated by the treatment laser beam. In other words, the whole pattern of the spots of the aiming beam are moved.

Herein, the timing of the aiming beam and the treatment laser beam is explained. FIG. 6 shows irradiation/non-irradiation of the aiming beam, irradiation/non-irradiation of the treatment laser beam, and input/non-input of the trigger signal. In a graph showing the aiming beam irradiation, the sections indicated by oblique lines represent that the aiming beam is continuously irradiated.

Until the trigger signal is input, the control unit 70 continues to irradiate the aiming beam. This allows the operator to recognize the state of FIG. 5A. In this state, check and alignment of the treatment site is performed.

When the trigger signal is input while the aiming beam is being irradiated to a first aiming irradiation region, the control unit 70 starts irradiation of the treatment laser beam to the irradiation region of the aiming beam. The treatment laser beam is sequentially irradiated by nine spots (the state of FIG. 5B). Assuming one shot is 20 ms, a total irradiation time T1 of the treatment laser beam is about 0.2 seconds. The control unit 70 does not irradiate the aiming beam while the treatment laser beam is being irradiated. As an alternative, the aiming beam may be irradiated during irradiation of the treatment laser beam.

When a series of irradiation of the treatment laser beam is terminated, the control unit 70 starts the irradiation of the aiming beam again. At that time, the irradiation position of the aiming beam is moved as shown in FIG. 5C. The aiming beam is irradiated at least for an irradiation time T2. This irradiation time T2 is set to the time allowing the operator to recognize the spot positions (herein, the whole pattern) of the aiming beam. In the present embodiment, since a subsequent trigger signal is input by the operator, the irradiation time T2 is determined depending on the operator. Accordingly, the control unit 70 waits for input of a trigger signal from restart of the irradiation of the aiming beam. Preferably, the control unit 70 is configured not to accept input of a trigger signal for the irradiation time T2. This allows the operator to easily check the irradiation position of the aiming beam. It is to be noted that the irradiation time T2 may be set by the operator. For instance, it is set in a range of several hundred milliseconds to a dozen seconds, e.g., to 0.1 seconds to 10 seconds, preferably, to 0.3 seconds to 2 seconds.

Thereafter, when the trigger signal is input while the aiming beam is being irradiated to a second aiming irradiation region, the control unit 70 sequentially irradiates the treatment laser beam to the aiming irradiation region of the aiming beam. The second aiming irradiation region is different in position on the fundus from the whole first aiming irradiation region.

After irradiation of the treatment laser beam to the first region (A1) is terminated in the above manner, the aiming beam is irradiated to the second region (A2) different from the first region (TL, M1) (the irradiation position of the aiming beam is moved). Since the irradiation position of the aiming beam (the spot pattern of the aiming beam) is changed below the irradiated region TL after a series of irradiation of the treatment laser beam, the operator does not need to move the observation optical system 30 and others every time when a series of irradiation of the treatment laser beam is terminated. This can save operator's trouble. Furthermore, the irradiation position of the aiming beam is shifted in correspondence with the spot interval D with respect to the irradiated position of the treatment laser beam, thereby improving the accuracy of aiming work (alignment) to a next treatment site.

Since the aiming beam is irradiated to the position different from the treatment-beam irradiated position after a series of irradiation of the treatment laser beam, the operator is allowed to easily check the state of the tissues in the position irradiated by the treatment laser beam.

The configuration that moves the irradiation pattern in a certain direction enables the operator to check the irradiation position every time a series of irradiation of the treatment laser beam is performed, thus facilitating irradiation of the treatment laser beam over a wide range. As compared to the configuration that irradiates the treatment laser beam at once over a wide range, the configuration of the present embodiment enables the operator to appropriately check the irradiation position of the treatment laser beam and easily cope with various situations during surgery.

The movement range of the irradiation position of the aiming beam (a limit of movement of the region A2) depends on the design of the irradiation optical system 40. Herein, this range is set so that a laser beam and others are not eclipsed (without vignetting) by the reflection mirror 46, that is, set to about 2 mm as an upper limit. In the present embodiment, if the movement range of spots of the aiming beam exceeds the upper limit (a part of the spots of the irradiation pattern exceeds the upper limit), the control unit 70 may also move the irradiation position of the aiming beam to the region TL (the initial treatment laser beam irradiation region), i.e., reset the irradiation position. Further, the control unit 70 may also be configured to reduce the number of spots so that the spots of the aiming beam fall within the upper limit if the movement range of the irradiation position of the aiming beam exceeds the upper limit. In this case, preferably, the spot interval is maintained.

In the above explanation, the movement range of the irradiation position of the aiming beam is set so that the position (coincident with the observation optical axis) corresponding to an original position of the optical scanner 50. However, the invention is not limited thereto. To effectively utilize the upper limit (limitation) of the irradiation optical system 40, it may be arranged to shift the start irradiation position of the aiming beam to the upper limit position of the optical system. For instance, in the automatic mode, the control unit 70 may shift the start irradiation position (corresponding to the region A1) of the aiming beam to the upper limit position of the optical system. Accordingly, the irradiation position of the aiming beam can be moved to as many positions in the up-and-down direction as possible, thereby enabling irradiation of the treatment laser beam at many sites. For instance, the aforementioned optical system can ensure a range of about 4 mm in the up-and-down direction.

Treatment operation by the apparatus configured as above using irradiation of the treatment laser beam will be explained. An operator sets the following items prior to the treatment.

The items to be set are the output power (e.g., 600 mW) of the treatment laser beam with the output power setting part 83, the pulse width (e.g., 20 ms) with the irradiation time setting part 84, the automatic mode with the movement mode setting part 85, the 3×3 square pattern and the spot interval D with the pattern setting part 86, the up-and-down direction with the movement direction setting part 87, the spot size (e.g., 200 μm) with the zoom lens 42, and others.

The operator places the contact lens CL in contact with the patient's eye E and observes, through the observation optical system 30, the fundus of the eye E illuminated by slit light emitted from the illumination optical system 60. Upon turn-on of an aiming switch not shown by the operator, the control unit 70 starts irradiation of the aiming beam. The operator makes alignment of the apparatus while observing the spots of the aiming beam presented in the square pattern. When the operator depresses the foot switch 81, the control unit 70 irradiates the treatment laser beam based on the trigger signal. After termination of a series of irradiation of the treatment laser beam, the control unit 70 irradiates the aiming beam (moves the irradiation position of the aiming beam) to a lower position (region) different from the irradiated spot position of the treatment laser beam and apart by the spot interval D.

In this state, upon depression of the foot switch 81, the control unit 70 irradiates the treatment laser beam in the spot positions just irradiated by the aiming beam. The control unit 70 then irradiates the aiming beam again to a lower region than the treatment-beam irradiated positions. The operator repeats those works to coagulate the treatment site in the up-and-down direction illuminated by the slit light. When the irradiation position of the aiming beam exceeds the upper limit of the movement range, the control unit 70 moves the irradiation position of the aiming beam to the position initially irradiated by the treatment laser beam in the up-and-down direction.

Thereafter, the operator moves the observation optical system 30 and others so that the spot position of the aiming beam under irradiation moves in the right-and-left direction (X direction), and repeats the above works. By those works, the treatment laser beam is irradiated over a wide range of the fundus.

In the above explanation, the irradiation of the treatment laser beam is triggered by the operator. However, the invention is not limited thereto. It is only necessary to move the irradiation position of the aiming beam after termination of a series of irradiation of the treatment laser beam, and perform subsequent irradiation of the treatment laser beam. For instance, it may be arranged that the control unit 70 triggers irradiation of the treatment laser beam and the operator stops the irradiation of the treatment laser beam.

To be concrete, an irradiation stop signal is input by the foot switch 81 serving as the signal input unit. Further, after a series of irradiation of the treatment laser beam is terminated and then the irradiation position of the aiming beam is moved, the control unit 70 suspends the irradiation of the treatment laser beam only for the irradiation time T2 and waits until the irradiation stop signal is input. The irradiation time T2 is the time allowing the operator to see the irradiation position of the aiming beam. This is an irradiation moratorium period. The irradiation time T2 is set at 0.1 to 3 seconds, preferably 0.3 to 1.5 seconds, more preferably 0.3 to 1.0 seconds. In this embodiment, 0.5 seconds is set.

The above configuration may be divided into two modes so that the operator chooses either one. For example, the display 82 is provided with an irradiation mode setting part. The irradiation modes include a first irradiation mode (a semiautomatic mode) of waiting for an irradiation signal from the foot switch 81 after moving the irradiation position of the aiming beam and a second irradiation mode (an automatic shot mode) of waiting for the irradiation stop signal from the foot switch 81 after moving the irradiation position of the aiming beam.

In the above explanation, the treatment laser beam is irradiated from the n-th spot to the m-th spot and then the irradiation position of the aiming beam is moved. Specifically, the treatment laser beam is irradiated from a start spot to a last spot in the 3×3 square pattern and then the aiming beam is moved. However, the invention is not limited to this configuration.

For irradiation of the treatment laser beam based on the irradiation pattern, it is necessary to allow an operator to check the position of spots (unirradiated spots) different from the treatment-beam irradiated spots after the treatment laser beam is irradiated to a plurality of spots.

For instance, the n-th spot position and the m-th spot position in the irradiation pattern are not necessarily the start and the last of all the spots of the irradiation pattern. An alternative is to irradiate the treatment laser beam at n-th to m-th spots (a partial region) of a part of the irradiation pattern and then move the aiming beam.

An example of a 9×3 square pattern is explained. The control unit 70 is configured to sequentially irradiate a treatment laser beam in the 9×3 square pattern, from first to ninth spots (a spot on $1^{st}$ row and $1^{st}$ column to a spot on $3^{rd}$ row and $3^{rd}$ column), from tenth to eighteenth spots, and from nineteenth to twenty-seventh spots. Based on the setting of the 9×3 square pattern, the control unit 70 initially irradiates the aiming beam in the 9×3 square pattern. Specifically, the control unit 70 irradiates the aiming beam to the first to ninth spot positions to prompt the operator to make treatment.

Upon receipt of the trigger signal input by the operator, the control unit 70 irradiates the treatment laser beam to a sequence of the first to ninth spot positions. Then, the control unit 70 irradiates the aiming beam to the tenth to eighteenth spot positions (moves the aiming beam irradiation positions). Based on the trigger signal, the control unit 70 irradiates the treatment laser beam to a sequence of the tenth to eighteenth spot positions. Successively, the control unit 70 irradiates the aiming beam to the nineteenth to twenty-seventh spot positions. The aiming rule in this case is set in association with the n-th to m-th spots. Accordingly, even when the irradiation pattern including a number of spots (a wide irradiation range) is selected, partial irradiation of the aiming beam makes it easy for the operator to see aiming beam spots.

In the above explanation, the movement direction of the irradiation position of the aiming beam is set to the up-and-down direction and the right-and-left direction, but it not limited thereto. The movement direction may be set to an arbitrary angle. Further, the advancing direction may be any direction. The movement direction may also include a plurality of patterns. For instance, when the irradiation position of the aiming beam is to be moved in the up-and-down direction, if the movement range exceeds the upper limit, the irradiation position may be moved instead in the right-and-left direction. In this case, the control unit 70 moves the irradiation position of the aiming beam (and the treatment laser beam) from above to below down to a lower limit. When the irradiation position reaches the lower limit, the control unit 70 moves the irradiation position to the right, and then from below to above. In this way, the irradiation position of the aiming beam is moved in a zigzag manner. The movement width in a lateral direction is preferably set to correspond to the width of the slit light.

In the above explanation, the movement position of the aiming beam is set so that the moved aiming beam spots are adjacent to and apart by the spot interval from the irradiated spots of the treatment laser beam, but is not limited thereto. The position of the aiming beam after movement is not necessarily adjacent. It is only necessary to move the aiming beam so that the spots are arranged in a grid form corresponding to the spot interval. Taking the configuration shown in FIG. 5B as an example, to be concrete, after irradiation of the treatment laser beam to the region TL, the irradiation position of the aiming beam is moved lower than the region A2. This skips the region corresponding to the irradiation pattern. Thus, dispersion of heat in the irradiation position of the treatment laser beam can be expected.

Although the above explanation shows that the irradiation position of the aiming beam is moved so that the spots are arranged in a grid form corresponding to the spot interval in a predetermined direction after a series of irradiation of the treatment laser beam, the invention is not limited thereto. It is only necessary to move the spot position of the aiming beam after a series of irradiation of the treatment laser beam. As another alternative, the spot position of the aiming beam may be moved to a previously set position.

The staggered pattern in the above explanation is configured so that the number of spots is equal in row and in column, but it is not limited thereto. Any spot configuration may be adopted as long as the spot interval between the spots is uniform in the up-and-down direction and in the oblique direction. For instance, a spot configuration of a staggered pattern having a hexagonal outline may be adopted. To evenly arrange such staggered patterns without gaps, the spots have to be moved not only in the up-and-down and right-and-left directions but also in the oblique direction.

In the above explanation, the optical scanner 50 is also used as the movement unit. The movement unit is not limited thereto and may be any configuration if only it can move the irradiation positions of treatment laser beam and aiming beam. For instance, the movement unit may be configured by tilting (rotating) the reflection mirror 46 in the X and Y directions. Furthermore, the irradiation optical system 40 may be provided with another optical scanner, a lens moving unit, and others as the movement unit. The movement unit may also be achieved by moving the slit lamp (the observation optical system 30 and others).

In the above explanation, the movement mode setting part 85, movement direction setting part 87, pattern setting part 86, and spot interval setting part 86b are not necessarily required. The setting of the apparatus 100 may be made in advance in a manufacturer.

In the above explanation, the presence/absence of the treatment laser beam and the presence/absence of the aiming beam are controlled by turn-on/off of the light sources. However, the present invention is not limited thereto as long as irradiation and non-irradiation of the treatment laser beam and others to the spot positions can be controlled. A shield means such as a shutter may also be used. As another alternative, an optical path deflecting means such as an optical scanner may also be used.

In the above explanation, the treatment laser beam is irradiated only one time to one spot position. The invention is not limited thereto and may adopt any configuration if only photocoagulation treatment of a fundus can be performed. For instance, a treatment laser beam having a short pulse width may be irradiated several times to one spot position at intervals having a predetermined stop (non-irradiation) period. In this case, minimally invasive photocoagulation treatment can be expected. In this case, adjacent spots are not necessarily required to be apart from each other.

In the above explanation, the treatment laser beam is irradiated to the fundus to perform photocoagulation treatment. However, the invention is not limited thereto and may be applied to any treatments achieved by performing treatment by irradiating a treatment laser beam to the tissues of a patient's eye. For example, the invention may also be applied to selective laser fiber meshwork angioplasty (SLT). In this case, the irradiation position of the aiming beam is moved along a gonioangle of a patient's eye.

In the above explanation, a plurality of spots of treatment laser beam are sequentially irradiated based on the irradiation pattern, but the invention is not limited thereto. The invention may include a mode (a single mode) of designating the position of a spot of treatment laser beam per one shot by an operator or others to irradiate the treatment laser beam.

When the irradiation position of the aiming beam with respect to a treatment site is to be controlled in different manners before and after irradiation of the treatment laser beam as shown in the automatic mode of the above embodiment, it is conceivable to control the irradiation position of the aiming beam to allow an operator to grasp the whole target region to be irradiated based on all the set irradiation patterns. For instance, it is possible to irradiate the aiming beam to the irradiation target position corresponding to an irradiation pattern (irradiation region) of the treatment laser beam to be performed next time and also to irradiate the aiming beam to an outer circumferential portion (e.g., four corners) allowing grasping of the whole area of the set irradiation target region.

The above explanations are mere examples and the present invention is not limited to the above. The invention may be embodied in other specific forms without departing from the essential characteristics thereof.

REFERENCE SIGNS LIST

10 Laser source unit
20 Optical fiber
30 Observation optical system
40 Laser irradiation optical system
50 Optical scanner
60 Illumination optical system
70 Control unit
80 Operation unit
100 Ophthalmic laser treatment apparatus

The invention claimed is:

1. An ophthalmic laser treatment apparatus including:
an irradiation optical system including an optical scanner for two-dimensionally scanning a spot of a treatment laser beam from a laser light source and a spot of an aiming beam from an aiming light source on a tissue of a patient's eye;
a control unit configured to control the irradiation optical system to irradiate the treatment laser beam to a spot position based on an irradiation pattern in which a plurality of spots for irradiation of the treatment laser beam are arranged, the control unit being arranged to control the irradiation optical system based on an aiming rule associated with the irradiation pattern to irradiate the aiming beam to the spot position to indicate the spot position for irradiation of the treatment laser beam; and an irradiation position moving unit configured to move an irradiation position of the treatment laser beam and the aiming beam,
wherein the control unit controls to:
irradiate the aiming beam at a first region, the first region having a shape of a two-dimensional matrix defined by the irradiation pattern, the first region including a first sequence of spots from a n-th spot position (n is a natural number) to a m-th spot position (m is a larger natural number than n);
irradiate the treatment laser beam at the first sequence of spots;
after irradiation of the first sequence of spots by the treatment laser beam has been terminated, control the irradiation position moving unit and automatically shift, based on the aiming rule, irradiation of the aiming beam from toward the first region to toward a second region, the second region also having the shape of a two-dimensional matrix defined by the irradiation pattern, the second region having a location different from that of the first region and not overlapping the first region, the second region including a sequence of spots different from the first sequence of spots based on pre-set instructions; and
irradiate the treatment laser beam at the second sequence.

2. The ophthalmic laser treatment apparatus according to claim 1, wherein the control unit moves the irradiation position of the aiming beam in a predetermined direction.

3. The ophthalmic laser treatment apparatus according to claim 1, wherein the irradiation pattern is a pattern consisting of spots arranged in a grid form.

4. The ophthalmic laser treatment apparatus according to claim 1, further including a spot interval input unit to input a spot interval of the irradiation pattern,
wherein the control unit moves the irradiation position of the aiming beam so that the spots of the aiming beam are arranged in association with the spot interval based on the spot interval input by the spot interval input unit.

5. The ophthalmic laser treatment apparatus according to claim 4, wherein the control unit irradiates the aiming beam so that an edge of the spot of the aiming beam based on the aiming rule is located at a position apart by the spot interval from an edge of the irradiated spot of the treatment laser beam.

6. The ophthalmic laser treatment apparatus according to claim 1, further including a movement direction input unit to input a movement direction of the irradiation position of the aiming beam to be moved by the movement unit,
wherein the control unit controls the irradiation position moving unit based on the movement direction input by the movement direction input unit.

7. The ophthalmic laser treatment apparatus according to claim 1, wherein the irradiation position moving unit is used as the optical scanner.

8. The ophthalmic laser treatment apparatus according to claim 1, further including a signal input unit to input a signal to trigger irradiation of the treatment laser beam,
wherein the control unit is configured to:
irradiate the treatment laser beam to a spot position corresponding to the irradiation pattern in the first sequence based on a first trigger signal input by the signal input unit and then control the irradiation position moving unit and irradiate the aiming beam to the second sequence, and irradiate the treatment laser beam to the spot position corresponding to the irradiation pattern in the second sequence based on a second trigger signal input by the signal input unit.

9. The ophthalmic laser treatment apparatus according to claim 8, wherein the signal input unit is an operation unit to be operated by an operator.

10. The ophthalmic laser treatment apparatus according to claim 8, further including a second signal input unit to input a signal to stop irradiation of the treatment laser beam, the second signal input unit being operated by an operator,
wherein the signal input unit is the control unit,
the control unit is configured to:
irradiate the aiming beam based on the aiming rule after a series of irradiation of the treatment laser beam, and wait for a stop signal from the second signal input unit for a predetermined time while the aiming beam is being irradiated, and
stop irradiation of the treatment laser beam when the control unit receives the stop signal from the second signal input unit or start irradiation of the treatment laser beam when the control unit receives no stop signal from the second signal input unit.

11. The ophthalmic laser treatment apparatus according to claim 1, further including a movement mode setting unit to set a mode of moving the irradiation position of the aiming beam after a series of irradiation of the treatment laser beam, the movement mode setting unit including a first movement mode of enabling movement of the irradiation position of the aiming beam by the control unit and a second movement mode of disabling movement of the irradiation position of the aiming beam by the control unit, and
the control unit is configured to move the irradiation position of the aiming beam after a series of irradiation of the treatment laser beam when the first movement mode is set by the movement mode setting unit or irradiate the aiming beam to the irradiated spot position of the treatment laser beam after a series of irradiation of the treatment laser beam when the second movement mode is set by the movement mode setting unit.

12. The ophthalmic laser treatment apparatus according to claim 1, wherein the n-th spot position is a start spot position in the irradiation pattern and the m-th spot position is a last spot position in the irradiation pattern.

13. The ophthalmic laser treatment apparatus according to claim 1, wherein the direction to move the irradiation position of the aiming beam after a series of irradiation of the treatment laser beam by the control unit corresponds to a longitudinal direction of slit illumination light.

14. The ophthalmic laser treatment apparatus according to claim 1, wherein the first region and the second region each include a plurality of spots in a first direction and a plurality of spots in a second direction different from the first direction.

15. A ophthalmic laser treatment apparatus including:
an irradiation optical system including an optical scanner for two-dimensionally scanning a spot of a treatment laser beam from a laser light source and a spot of an aiming beam from an aiming light source on a tissue of a patient's eye;
a setting unit to set an irradiation pattern in which a plurality of spots for irradiation of the treatment laser beam are arranged in predetermined groups, each group including spots for radiation in a predetermined form, the setting unit being configured to set a direction for changing irradiation of the treatment laser beam and the aiming beam from toward a first group of the predetermined groups to toward a second group of the predetermined group after the spots included in the first group have been irradiated by the treatment laser beam, the second group being different from the first group, the first group forming a first region, the first region having a shape of a two-dimensional matrix defined by the irradiation pattern, the second group forming a second region, the second region also having the shape of a two-dimensional matrix defined by the irradiation pattern, the second region having a location different from that of the first region and not overlapping the first region;
a control unit configured to control the irradiation optical system to irradiate the treatment laser beam to a spot position in a group based on the set irradiation pattern of the group, the control unit being configured to control the irradiation optical system based on an aiming rule associated with the irradiation pattern to irradiate the aiming beam to the spot position to indicate the spot position for irradiation of the treatment laser beam; and
an irradiation position moving unit configured to move an irradiation position of the treatment laser beam and the aiming beam,
wherein the setting unit sets the irradiation pattern consisting of the plurality of spots arranged in a predetermined form as one group, and combines the predetermined groups to set an irradiation pattern that covers a wider area than the irradiation pattern defined as one group,
the control unit:
controls irradiation of the aiming beam to the first group based on the aiming rule associated with the irradiation pattern of the first group,
after irradiation of the treatment laser beam based on the irradiation pattern of the first group has been terminated, controls the irradiation optical system to change irradiation of the treatment laser beam and the aiming beam from toward the first group to toward the second group based on the direction set by the setting unit and to irradiate the aiming beam based on the aiming rule associated with the irradiation pattern of the second group.

16. The ophthalmic laser treatment apparatus according to claim 15, wherein the first group and the second group each include a plurality of spots in a first direction and a plurality of spots in a second direction different from the first direction.

* * * * *